United States Patent
Al-Khairy (10) Patent No.: US 12,196,548 B2
(45) Date of Patent: Jan. 14, 2025

(54) METHOD AND SYSTEM FOR SIZING A CHIP IN ENGINE FLUID

(71) Applicant: PRATT & WHITNEY CANADA CORP., Longueuil (CA)

(72) Inventor: Issam Al-Khairy, Verdun (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 212 days.

(21) Appl. No.: 17/404,057

(22) Filed: Aug. 17, 2021

(65) Prior Publication Data
US 2023/0054919 A1    Feb. 23, 2023

(51) Int. Cl.
*G01B 7/02* (2006.01)
*G01N 19/06* (2006.01)
*G01N 33/28* (2006.01)
*H03K 17/95* (2006.01)

(52) U.S. Cl.
CPC .............. *G01B 7/02* (2013.01); *H03K 17/95* (2013.01)

(58) Field of Classification Search
CPC ....... G01M 17/00; G01N 15/02; G01N 15/10; G01N 15/1031; G01N 27/04; G01N 27/06; G01N 33/2888; G01N 33/2858; G01B 7/02; H03K 17/95; G01V 3/08; G01V 3/02
See application file for complete search history.

(56) References Cited

U.S. PATENT DOCUMENTS

| | | | |
|---|---|---|---|
| 4,070,660 A * | 1/1978 | Tauber | G01N 33/2858 340/631 |
| 4,598,280 A | 7/1986 | Bradford | |
| 5,152,372 A | 10/1992 | Volman | |
| 5,406,208 A | 4/1995 | Bitts | |
| 5,742,234 A | 4/1998 | Owen | |
| 9,874,510 B2 | 1/2018 | Kudrna | |
| 10,197,488 B2 | 2/2019 | Youssef | |
| 10,317,354 B2 | 6/2019 | Ricci et al. | |
| 10,866,201 B2 | 12/2020 | Best | |
| 11,448,636 B2 | 9/2022 | Padilla Martinez | |
| 11,906,504 B2 | 2/2024 | Szczesnowicz et al. | |
| 2018/0106196 A1 * | 4/2018 | Kelly | F01D 25/18 |
| 2018/0364141 A1 * | 12/2018 | Youssef | G01V 3/08 |
| 2019/0257777 A1 | 8/2019 | Ricci et al. | |
| 2023/0152297 A1 | 5/2023 | Riverin | |

FOREIGN PATENT DOCUMENTS

GB     2559877 A     8/2018

OTHER PUBLICATIONS

European Patent Office, Communication re. extended European search report for European patent application No. 22190863.5, Jan. 16, 2023.

* cited by examiner

*Primary Examiner* — Son T Le
(74) *Attorney, Agent, or Firm* — Norton Rose Fulbright Canada LLP

(57) ABSTRACT

Methods and systems of estimating a size of a chip in engine fluid of an engine are provided. One method comprises detecting the chip at a magnetic chip detector immersed in the engine fluid, burning the chip by Joule heating using a single delivery of electric current through the chip via the first and second terminals of the magnetic chip detector, determining an amount of energy consumed to burn the chip, and estimating the size of the chip based on the amount of energy consumed to burn the chip.

20 Claims, 8 Drawing Sheets

| CHIP ID | ENERGY CONSUMED | CHIP SIZE |
|---|---|---|
| C1 | EC1 | CS1 |
| C2 | EC2 | CS2 |
| C3 | EC3 | CS3 |

FIG-8

METHOD AND SYSTEM FOR SIZING A CHIP IN ENGINE FLUID

TECHNICAL FIELD

The disclosure relates generally to health monitoring of engines, and more particularly to characterizing chips in fluids of aircraft engines.

BACKGROUND

A magnetic chip detector is commonly found in a lubrication system of an aircraft engine to detect the presence of chips in the lubrication fluid. The chip detector is immersed in the lubrication fluid so as to be exposed to the chips carried by the lubrication fluid. The presence of chips in the lubrication fluid may indicate a developing and/or impending mechanical problem exhibiting excessive wear of one or more components of the aircraft engine interacting with the lubrication system. When chips are collected by the chip detector, a gap between two electric terminals is eventually bridged so as to provide electric continuity and cause an indication (e.g., alarm) to be provided to an operator of the aircraft so that an appropriate action can be taken if necessary. The presence of metal chips in engine fluid can be indicative of an engine health condition and it is desirable to improve chip detection in aircraft engines.

SUMMARY

In one aspect, the disclosure describes a method of estimating a size of a chip in engine fluid of an engine. The method comprises:
  detecting the chip at a magnetic chip detector immersed in the engine fluid, the chip providing electric communication between a first terminal and a second terminal of the magnetic chip detector;
  after detecting the chip, burning the chip by Joule heating using a single delivery of electric current through the chip via the first and second terminals of the magnetic chip detector;
  determining an amount of energy consumed to burn the chip in the single delivery of electric current; and
  estimating the size of the chip based on the amount of energy consumed to burn the chip.

In another aspect, the disclosure describes a method of detecting and sizing a chip in lubrication fluid of an engine. The method comprises:
  detecting a presence of one or more particles at a magnetic chip detector immersed in the lubrication fluid, the one or more particles providing electric communication between a first terminal and a second terminal of the magnetic chip detector;
  after detecting the presence of the one or more particles at the magnetic chip detector, causing disintegration of the one or more particles by Joule heating by continuously driving electric current through the one or more particles via the first and second terminals for a uninterrupted duration;
  determining an amount of energy consumed to cause disintegration of the one or more particles by Joule heating;
  when the amount of energy is smaller than a prescribed energy value, determining that the one or more particles are fuzz; and
  when the amount of energy is greater than the prescribed energy value:
    determining that the one or more particles are a chip; and
    estimating a size of the chip based on the amount of energy consumed to cause disintegration of the chip.

In a further aspect, the disclosure describes a system for detecting and sizing a chip in lubrication fluid of an engine. The system comprises:
  a magnetic chip detector immersible in a lubrication fluid of the engine, the chip detector including a first terminal and a second terminal spaced apart from the first terminal;
  an electric power source connectable to the magnetic chip detector to apply a voltage between the first and second terminals of the magnetic chip detector;
  one or more data processors; and
  non-transitory machine-readable memory storing instructions executable by the one or more data processors and configured to cause the one or more data processors to:
    detect a presence of one or more particles at the magnetic chip detector immersed in the lubrication fluid based on a sensed resistance between the first and second terminals of the chip detector;
    after detecting the presence of the one or more particles at the magnetic chip detector, cause burning of the one or more particles by Joule heating using a single delivery of electric current through the one or more particles via the first and second terminals of the magnetic chip detector;
    determine an amount of energy consumed to burn the one or more particles in the single delivery of electric current;
    when the amount of energy consumed to burn the one or more particles is indicative of the one or more particles being a chip, estimate a size of the chip based on the amount of energy consumed to burn the one or more particles.

Further details of these and other aspects of the subject matter of this application will be apparent from the detailed description included below and the drawings.

DESCRIPTION OF THE DRAWINGS

Reference is now made to the accompanying drawings, in which.

DETAILED DESCRIPTION

The present disclosure relates to systems and methods for detecting and sizing chips in engine (e.g., lubrication, cooling) fluids. In some embodiments, the systems and methods described herein may help assess a condition of an engine by determining the size(s) and/or the detection frequency of one or more chips detected in the engine fluid. In some embodiments, the systems and methods described herein may drive current through a chip detected in order to cause Joule heating and burning of the chip. The current delivered to the chip and the applicable time duration required to cause burning of the chip may be used to determine an amount of energy used to burn the chip. The amount of energy used may then be related to an associated size of the chip. The size and/or frequency of the detected chips(s) may then be used to determine whether any (e.g., corrective) action such as an inspection and/or maintenance activity is required.

In some embodiments, the systems and methods described herein may also reduce the likelihood of nuisance detections (e.g., alarms) associated with the accumulation of acceptable smaller/fine magnetic debris/particles, commonly referred to as "fuzz" at a magnetic chip detector immersed in lubrication fluid. Some fuzz can be generated during the normal operation of an aircraft engine and may not necessarily be indicative of a developing or impending mechanical problem. For example, such fuzz can normally be generated during the initial period (e.g., a few hundred hours) of operation of an aircraft engine following initial entry into service or following extensive maintenance such as an overhaul. This initial period is also known as the engine's "break-in" period. Detections caused by the accumulation of the acceptable and relatively harmless fuzz, during the break-in period for example, oppose the design intent of the magnetic chip detector and are undesirable since they do not provide an accurate indication of a possible developing or impending problem. In some embodiments, the systems and methods described herein may rely on the amount of energy used to burn the accumulated particle(s) in order to discriminate between fuzz and more worrisome larger chips that may be carried by the lubrication fluid.

Aspects of various embodiments are described through reference to the drawings. Even though the description below is provided in relation to lubrication fluid, it is understood that some embodiments of the systems and methods described herein may also be used on other types of engine fluids such as engine coolant for example.

The term "connected" may include both direct connection (in which two elements that are connected to each other contact each other) and indirect connection (in which at least one additional element is located between the two elements).

The term "substantially" as used herein may be applied to modify any quantitative representation which could permissibly vary without resulting in a change in the basic function to which it is related.

Figure 1:
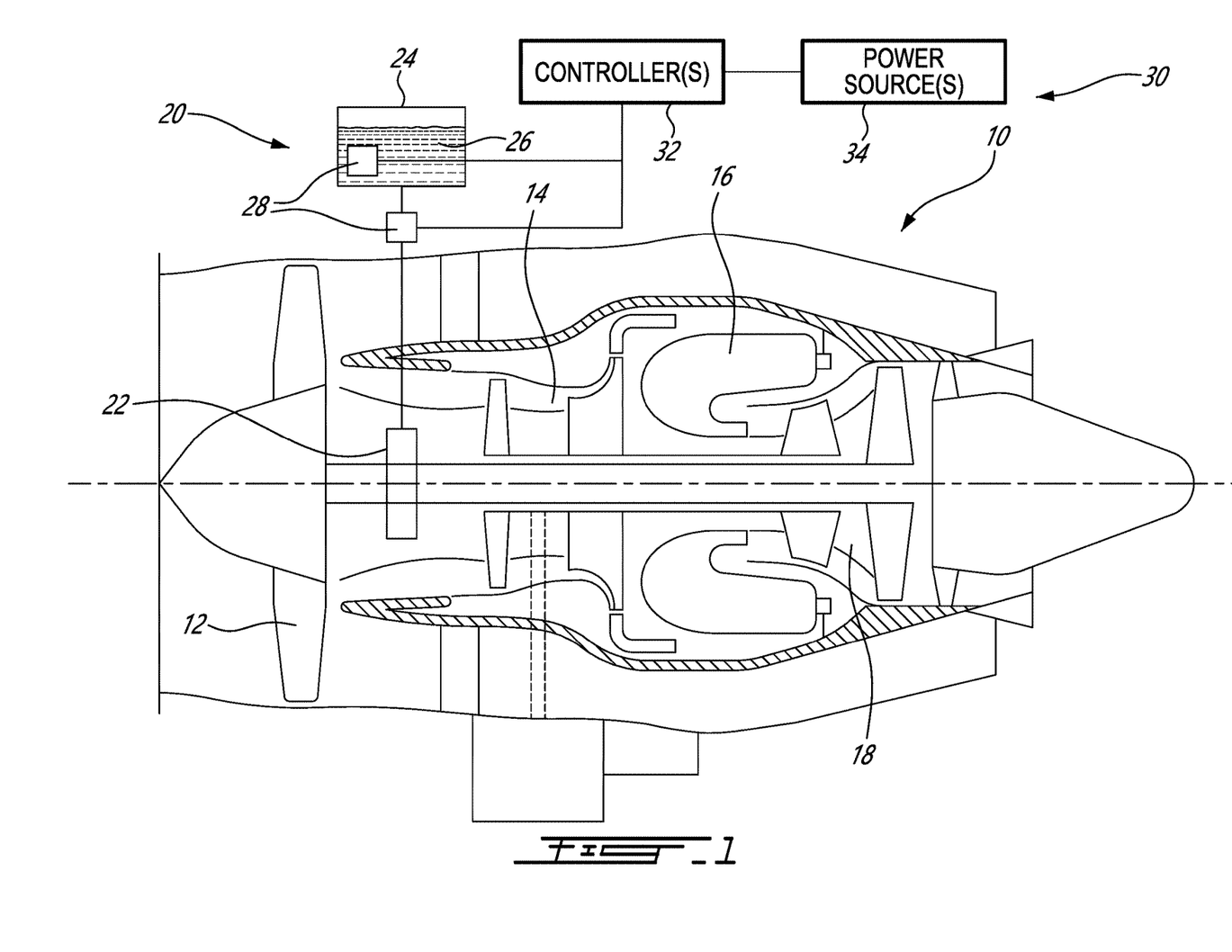
FIG. 1 is a schematic axial cross-section view of a turbofan gas turbine engine and a chip sizing system as described herein.

FIG. 1 is a schematic axial cross-section view of aircraft engine 10 (referred hereinafter as "engine 10") of a turbofan gas turbine engine preferably provided for use in subsonic flight, generally comprising, in serial flow communication, fan 12 through which ambient air is propelled, multistage compressor 14 for pressurizing the air, combustor 16 in which the compressed air is mixed with fuel and ignited for generating an annular stream of hot combustion gases, and turbine section 18 for extracting energy from the combustion gases. Engine 10 may be mounted to an aircraft and used to propel such aircraft. Even though FIG. 1 shows engine 10 being of the turbofan type, it is understood that aspects of the present disclosure are also applicable to other (e.g., turboshaft, turboprop, internal combustion) types of aircraft engines.

Engine 10 may include lubrication system 20 shown schematically and partially in FIG. 1. Lubrication system 20 may serve to lubricate, cool and clean one or more lubrication loads 22 such as bearings and gears of engine 10. Lubrication system 20 may include tank 24 and other components such as one or more pumps, one or more valves, and one or more filters. Tank 24 may be a reservoir containing a supply of lubrication fluid 26 such as oil for use by lubrication system 20. Lubrication system 20 may include one or more magnetic chip detectors (MCDs) 28. For example, lubrication system 20 may include a single MCD 28 or a plurality of MCDs 28 disposed at different locations within lubrication system 20. MCD 28 may be at least partially immersed in lubrication fluid 26 during operation. For example, MCD 28 be disposed inside tank 24, inside a gearbox, or in a scavenge line.

Chip detection and sizing system 30 (referred hereinafter as "system 30") may be associated with and/or may be part of engine 10. System 30 may include controller 32 operatively connected to MCD 28. System 30 may include electric power source 34 operatively connected to controller 32. System 30 may optionally include other components as explained below.

Figure 2:
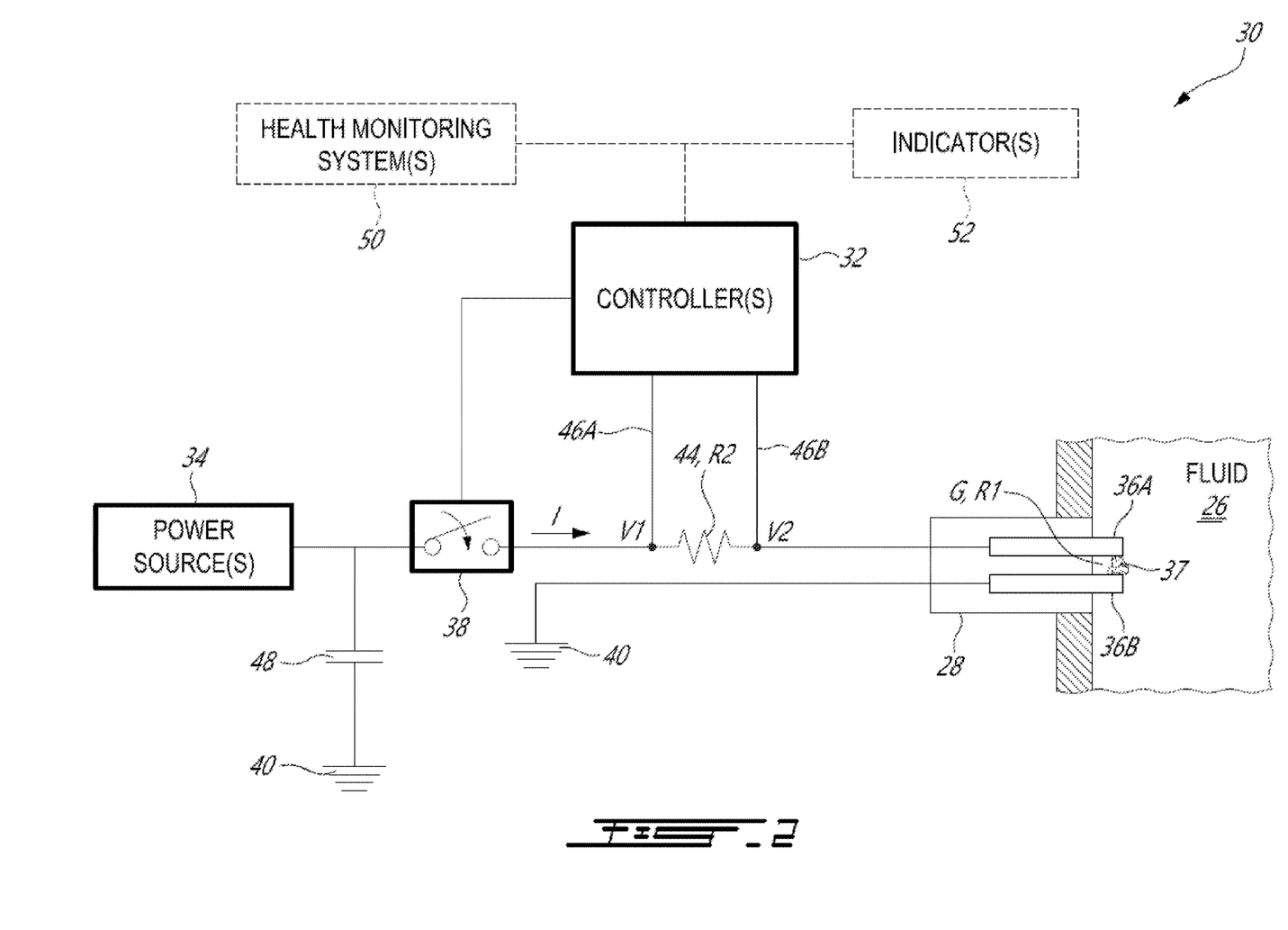
FIG. 2 is an exemplary schematic representation of the chip sizing system associated with the engine of FIG. 1.

FIG. 2 is an exemplary schematic representation of system 30, which may be associated with or part of engine 10. System 30 may include MCD 28 immersible in lubrication fluid 26 of engine 10. In some embodiments, MCD 28 may be of the type disclosed in U.S. Pat. No. 10,197,488 (Title: SYSTEMS AND METHODS FOR DETECTING CHIPS IN FLUID OF AIRCRAFT ENGINE), which is incorporated herein by reference. Other types of magnetic chip detectors may be suitable for use with system 30. For example, "radial gap" or "axial gap", also known as "disc type" magnetic chip detectors may be suitable for use with system 30. In reference to FIG. 2, MCD 28 may include two magnetic terminals 36A, 36B (prongs) that may be spaced apart and separated from each other by gap G. When one or more metallic and magnetic particles 37 (e.g., fuzz or chip(s)) that are carried by lubrication fluid 26 are attracted to terminals 36A, 36B and bridge gap G, electric communication (e.g., relatively low resistance or short-circuit) may be established between terminals 36A, 36B via particle(s) 37 accumulated between terminals 36A, 36B.

Electric power source 34 that may be connectable to MCD 28 via switch 38 (contactor). For example, power source 34 may be connectable to apply a voltage differential between terminals 36A, 36B and also drive current through particle(s) 37 when such particle(s) 37 establish electric communication between terminals 36A, 36B and across gap G. For example, first terminal 36A may be electrically connectable to power source 34 via switch 38, and second terminal 36B may be electrically connected to ground 40, which may provide a current return path. In some embodiments, power source 34 may include a direct current (DC) power bus of engine 10, or of an aircraft to which engine 10 is mounted. In some embodiments, power source 34 may include a battery. In some embodiments, power source 34 may also be used to power controller 32. In some embodiments, switch 38 may be part of controller 32 and electric current may be supplied to MCD 28 from power source 34 via controller 32. In some embodiments, power source 36 may have a voltage of about 28 volts for example.

Controller 32 may monitor electric resistance R1 across terminals 36A, 36B via electric connection 46B and ground 40 to which controller 32 may be electrically connected. When no particles are accumulated between terminals 36A, 36B, resistance R1 across terminals 36A, 36B may be relatively high (e.g., open-circuit, infinite). However, when particle(s) 37 is/are received in gap G and establish electric communication between terminals 36A, 36B, resistance R1 across terminals 36A, 36B may be relatively low (e.g., short-circuit). When monitoring resistance R1 across terminals 36A, 36B, the relatively low resistance R1 and/or the (e.g., sudden, sharp) reduction in resistance R1 across terminals 36A, 36B may signal to controller 32 that particle(s) 37 has/have been captured between terminals 36A, 36B. After making such determination, controller 32 may command switch 38 to close in order to initiate the burning of particle(s) 37 captured between terminals 36A, 36B.

Burning of particle(s) 37 may be conducted by driving electric current across gap G and through particle(s) 37 disposed between terminals 336A, 36B to conduct Joule heating. Joule heating is also known as resistive, resistance, or Ohmic heating, and is the process by which the passage of an electric current through a conductor produces heat.

In some embodiments, switch 38 may be kept closed and electric current I may be continuously driven into particle(s) 37 until the burning of particle(s) 37 has been sufficiently completed. Electric current I may be driven through particle(s) 37 as a single (sole) delivery (e.g., dose, pulse) of a duration suitable for completing the desired burning of particle(s) 37. For example, current I may be delivered to particle(s) 37 as a single, uninterrupted delivery to complete the desired burning of particle(s) 37 in one shot. Accordingly, the duration of the single delivery of electric current I may not be determined in advance and may vary from one accumulation of particle(s) 37 to another.

After the desired amount of burning of particle(s) 37 has been completed, controller 32 may command switch 38 to open to electrically disconnect terminals 36A, 36B from power source 34. Burning of particle(s) 37 may include the at least partial breakdown (e.g., melting, disintegration, destruction) of particle(s) 37. In some embodiments, the burning may be determined to be complete when electric communication between terminals 36A, 36B is terminated due to the burning of particle(s) 37 for example. In such embodiments, the current flow across terminals 36A, 36B may be automatically stopped due to reaching of an open-circuit condition between terminals 36A, 36B. For example, the delivery of current I through particle(s) 37 may be ceased when the presence of particle(s) 37 between terminals 36A, 36B is no longer detected. For example, the delivery of current I through particle(s) 37 may be ceased when particle(s) 37 no longer establish electric communication between terminals 36A, 36B.

In some embodiments, adequate burning of particle(s) 37 may be deemed completed before reaching the open-circuit condition. For example, controller 32 may determine that the burning is complete when a prescribed electric resistance threshold (prescribed resistance value) across terminals 36A, 36B has been reached. Any suitable criterion may be programmed into controller 32 to determine when sufficient burning of particle(s) 37 is complete, and terminate the Joule heating. Controller 32 may command switch 38 to adopt the open position shown in FIG. 2 after the burning of particle(s) 37.

As explained below, controller 32 may determine the amount of energy consumed during the burning of particle (s) 37 for the purpose of characterizing particle(s) 37. The amount of energy consumed may be determined by sensing electric current I being driven through particle(s) 37 during the Joule heating. Current I may be sensed using a suitable current sensor connected in series with power source 34 and terminal 36A for example. Alternatively, current I may be determined by monitoring a voltage drop (i.e., V1–V2) across resistor 44 of a fixed known resistance R2. For example, voltages V1 and V2 may be measured using electric connections 46A, 46B using a suitable voltage sensor and current I may be computed using Ohm's law (I=(V1–V2)/R2).

Using current I delivered during the Joule heating of particle(s) 37 during the burning, the associated value(s) of resistance R1 across terminals 36A, 36B, and the duration of the delivery of current I, the energy consumed during the burning of particle(s) 37 may be computed by controller 32. For example, the energy consumed may be computed using the relationship: Energy Consumed=$I^2$R1*Duration. It is understood that the values of current I and resistance R1 may not be constant during the burning process and that controller 32 may consider temporal variations in current I and in resistance R1 in the determination of the energy consumed.

In some embodiments, system 30 may include one or more optional capacitor(s) 48 (referred hereinafter in the singular) that may be used to assist with the initial delivery of current I to particle(s) 37. Capacitor 48 may be electrically disposed between power source 34 and ground 40, and may also be connected in series with first terminal 36A for example. Capacitor 48 may assist in providing an initial surge of current I to particle(s) 37 if desired.

Tasks described herein may be performed entirely by controller 32 or may be shared by controller 32 and other devices. For example, some data collected by controller 32 may be communicated to health monitoring system 50 (referred hereinafter as "HMS 50") for further calculations and analysis. For example, the calculation of energy consumed may be performed by controller 32 or by HMS 50. For example, the estimation of the chip size based on the energy consumed during burning may be performed by controller 32 or by HMS 50. Based on the energy consumed and/or based on the chip size, controller or HMS 50 may determine whether or not some corrective action should be scheduled and carried out. If a corrective action is determined to be required, controller 32 or HMS 50 may, based on one or more rules, identify and select one or more applicable corrective actions. For example, such rules may be based on the historical data associated with engine 10, performance data associated with engine 10, the engine type, and/or predicted mechanism(s) of failure including bearing wear and gear degradation for example. Suitable corrective actions may include one or more inspection activities, maintenance activities (e.g., diagnostic, component replacement, overhaul), and/or decommissioning for example. Some corrective action(s) may be carried out by maintenance personnel.

In some embodiments, controller 32 and/or HMS 50 may be operatively connected to one or indicator(s) 52 (referred hereinafter in the singular) that may be used to alert maintenance personnel and/or the flight crew of the aircraft to which engine 10 is mounted. Controller 32 and/or HMS 50 may cause such alert to be generated based on sizing and/or frequency of particle(s) 37, and whether further action is required. In some embodiments, indicator 52 may be a suitable visual indicator such as an indicator light, gauge and/or display screen. In some embodiments, indicator 52 may be a suitable aural indicator such as a loudspeaker for example. Indicator 52 may be part of a flight deck of an aircraft and/or may be located at a ground (e.g., maintenance) facility for example.

Figure 3:
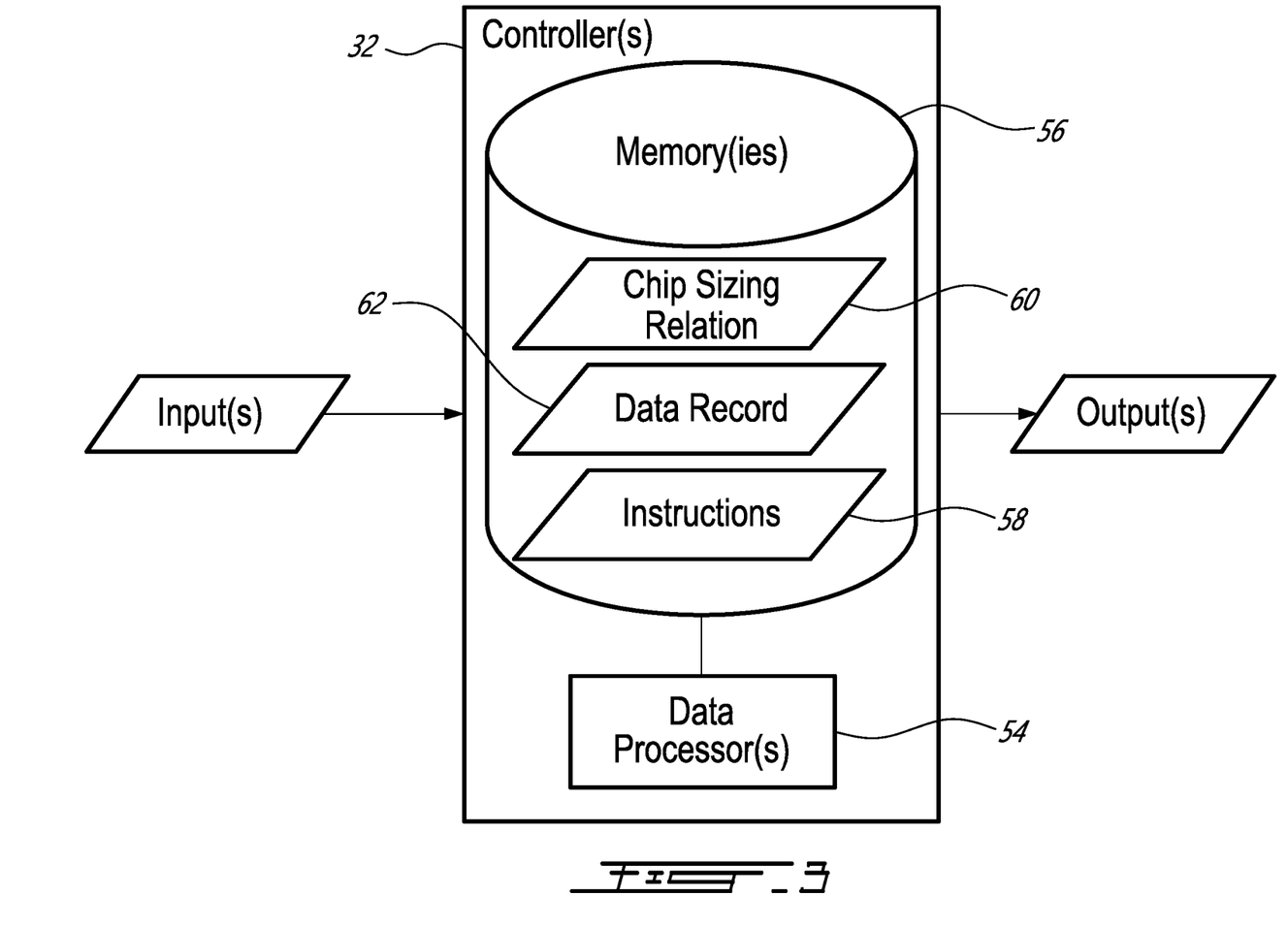
FIG. 3 is a schematic representation of an exemplary controller of the chip sizing system of FIG. 2.

FIG. 3 is a schematic representation of an exemplary controller 32 of system 30. In various embodiments, controller 32 may include or form part of a Full Authority Digital Engine Control (FADEC) which may, for example, include one or more digital computer(s) or other data processors, sometimes referred to as electronic engine controller(s) (EEC) and related accessories that control at least some aspects of performance of engine 10. Controller 32 may for example be configured to make decisions regarding the control of engine 10.

Controller 32 may include one or more data processors 54 (referred hereinafter as "processor 54") and non-transitory machine-readable memory 56. Controller 32 may be configured to regulate the operation of system 30 and optionally also control other aspects of operation of engine 10. Controller 32 may carry out additional functions than those described herein. Controller 32 may receive input(s), perform one or more procedures or steps defined by instructions 58 stored in memory 56 and executable by processor 54 to generate output(s). Processor 54 may include any suitable device(s) configured to cause a series of steps to be performed by controller 32 so as to implement a computer-implemented process such that instructions 58, when executed by controller 32 or other programmable apparatus, may cause the functions/acts specified in the methods described herein to be executed. Processor 54 may include, for example, any type of general-purpose microprocessor or microcontroller, a digital signal processing (DSP) processor, an integrated circuit, a field programmable gate array (FPGA), a reconfigurable processor, other suitably programmed or programmable logic circuits, or any combination thereof.

Memory 56 may include any suitable machine-readable storage medium. Memory 56 may include non-transitory computer readable storage medium such as, for example, but not limited to, an electronic, magnetic, optical, electromagnetic, infrared, or semiconductor system, apparatus, or device, or any suitable combination of the foregoing. Memory 56 may include a suitable combination of any type of machine-readable memory that is located either internally or externally to controller 32. Memory 56 may include any storage means (e.g. devices) suitable for retrievably storing machine-readable instructions 58 executable by processor 54.

Various aspects of the present disclosure may be embodied as systems, devices, methods and/or computer program products. Accordingly, aspects of the present disclosure may take the form of an entirely hardware embodiment, an entirely software embodiment or an embodiment combining software and hardware aspects. Furthermore, aspects of the present disclosure may take the form of a computer program product embodied in one or more non-transitory computer readable medium(ia) (e.g., memory 56) having computer readable program code (e.g., instructions 58) embodied thereon. Computer program code for carrying out operations for aspects of the present disclosure in accordance with instructions 58 may be written in any combination of one or more programming languages. Such program code may be executed entirely or in part by controller 32 or other data processing device(s). It is understood that, based on the present disclosure, one skilled in the relevant arts could readily write computer program code for implementing the methods described and illustrated herein.

Figure 7:
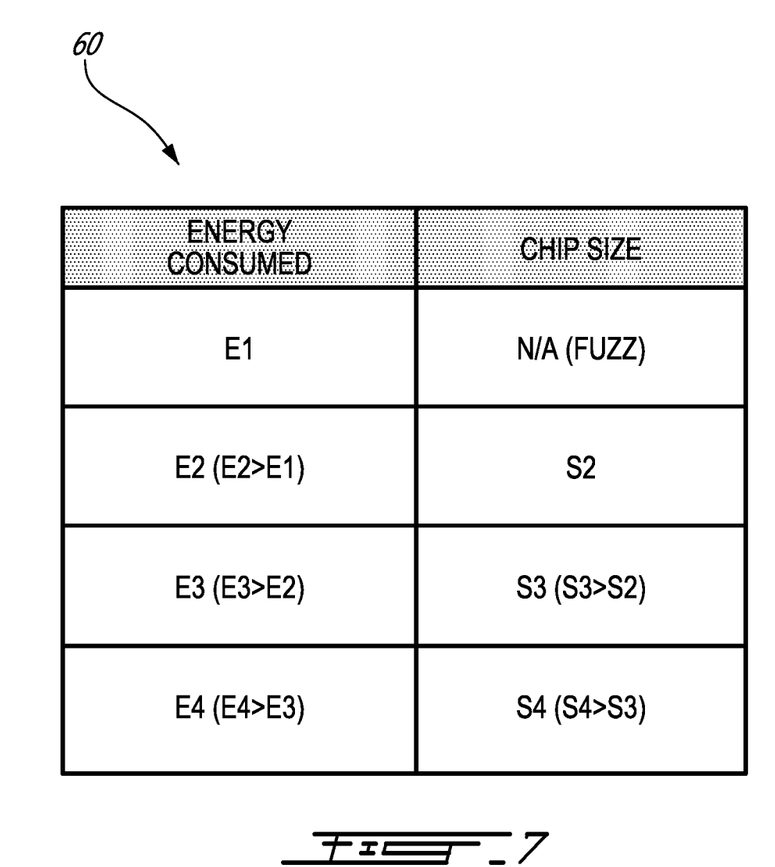
FIG. 7 is an exemplary look-up table that specifies a relation between energy consumed to burn a chip and chip size.

In some embodiment, memory 56 may also store chip sizing relation 60 which may define a relationship between estimated chip size and the energy consumed during burning of the chip. In some embodiments, chip sizing relation 60 may have the form of a look-up table as shown in FIG. 7, and may be used to infer a chip size based on the amount of energy consumed to burn particle(s) 37.

Figure 8:
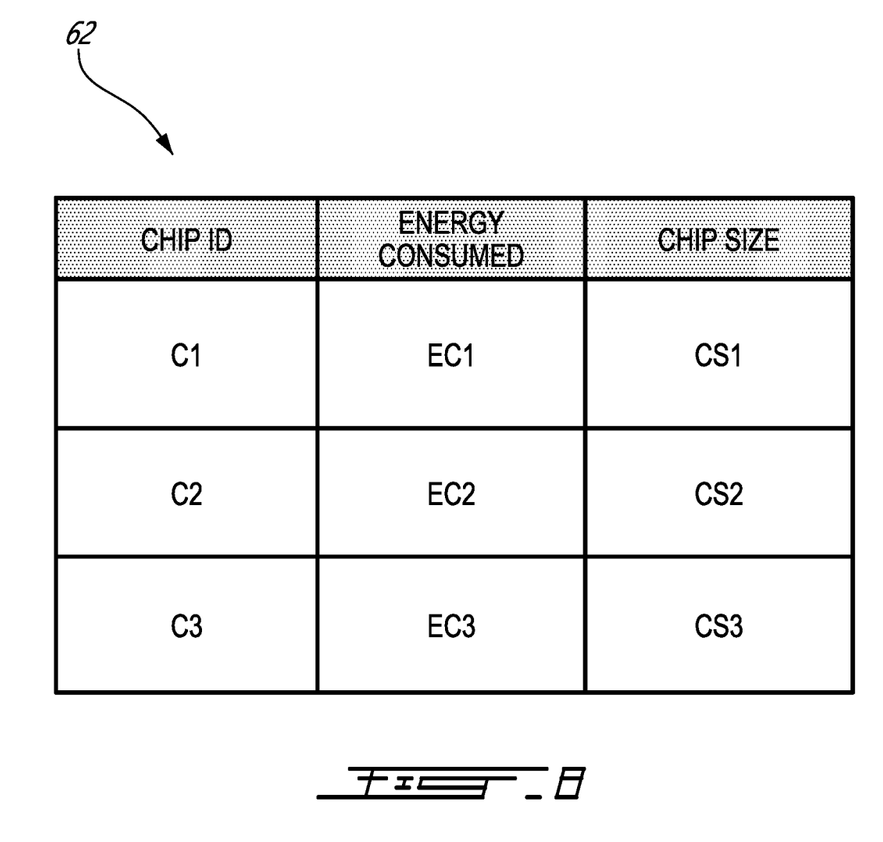
FIG. 8 is an exemplary data record constructed using the system of FIG. 2.

In some embodiment, memory 56 may also store data record 62 that may be constructed (e.g., populated) as particle(s) 37 are burned during the operation of system 30. Data record 62 may be used to record a log of particle(s) 37 that have been burned. Data record 62 may have the form as shown in FIG. 8. Data record 62 may be used by controller 32 and/or by HMS 50 for (e.g., statistical) analysis and used to asses a health condition of engine 10, and determine whether and/or what corrective action needs to be carried out.

Figure 4:
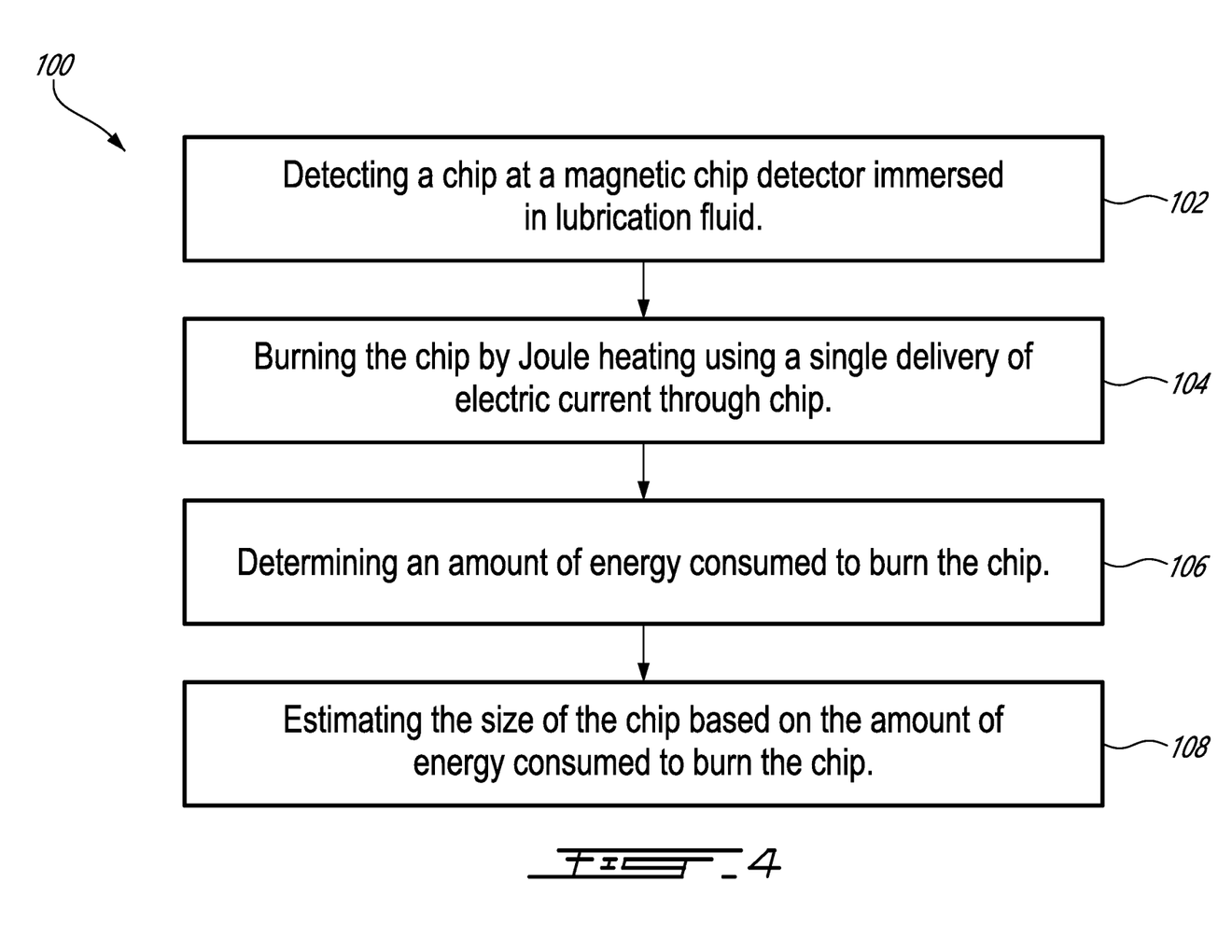
FIG. 4 is a flowchart of an exemplary method of sizing a chip detected in lubrication fluid of the engine of FIG. 1.

FIG. 4 is a flowchart illustrating an exemplary method 100 of estimating a size of a chip in lubrication fluid 26 or other fluid of engine 10 using MCD 28 or another chip detector. Method 100 may be performed using system 30 described herein or using another system. Aspects of method 100 may be combined with other methods or steps described herein. Method 100 may also include aspects of system 30. In various embodiments, method 100 may include:

detecting the chip at MCD 28 immersed in lubrication fluid 26 or other fluid (block 102), the chip providing electric communication between first terminal 36A and second terminal 36B of MCD 28;

after detecting the chip, burning the chip by Joule heating using a single delivery of electric current through chip via first terminal 36A and second terminal 36B of MCD 28 (block 104);

determining an amount of energy consumed to burn the chip in the single delivery of electric current (block 106); and estimating the size of the chip based on the amount of energy consumed to burn the chip (block 108).

In some embodiments of method 100, the burning of the chip by Joule heating may be automatically initiated by controller 32 for example after detecting the chip at MCD 28. In other words, the initiation of the burning of the chip by Joule heating may be initiated without intervention or involvement by the flight crew. Detecting the chip at MCD 28 may include detecting, between first terminal 36A and second terminal 36B, resistance R1 (shown in FIG. 2) at or below a low resistance threshold. In some embodiments, the low resistance threshold may be indicative of a short-circuit condition between first terminal 36A and second terminal 36B of MCD 28.

In some embodiments of method 100, the single delivery of electric current through the chip may be terminated when resistance R1 between first terminal 36A and second terminal 36B reaches or exceeds a high resistance threshold. In some embodiments, the high resistance threshold may be indicative of an open-circuit condition between first terminal 36A and second terminal 36B of MCD 28.

After estimating the size of the chip, method 100 may include selecting a maintenance activity to be conducted based on the size of the chip. Method 100 may include initiating the maintenance activity for engine 10 based on the estimated size of the chip. Initiating the maintenance activity may include causing an indication to be provided to the flight crew or to maintenance personnel via indicator 52 or via other means. In some embodiments, method 100 may include performing the maintenance activity. The maintenance activity may be performed by maintenance personnel. Method 100 may be repeated with one or more additional chips.

Figure 5:
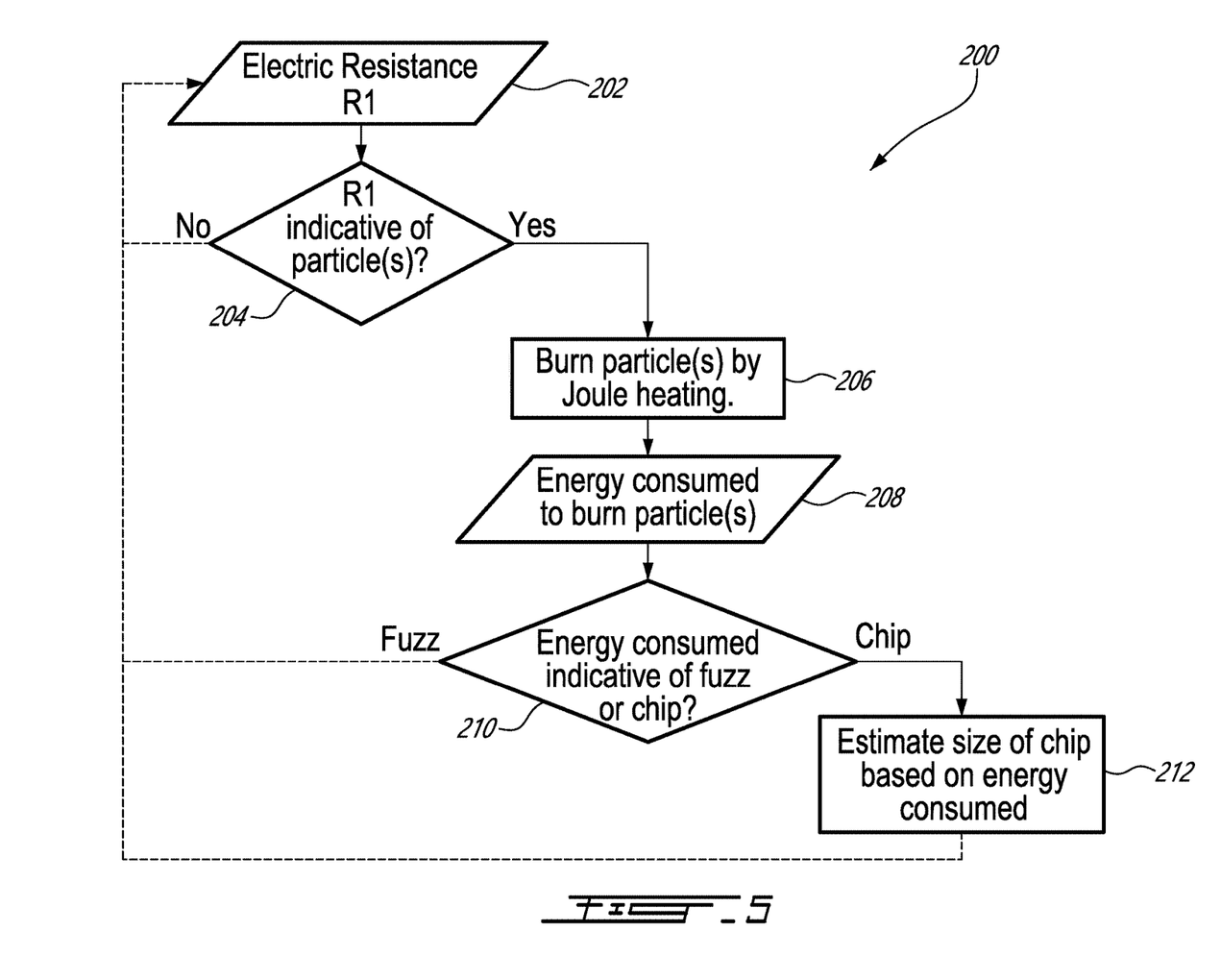
FIG. 5 is a flowchart of an exemplary method of detecting and sizing a chip in lubrication fluid of the engine of FIG. 1.

FIG. 5 is a flowchart illustrating an exemplary method 200 of detecting and sizing a chip in lubrication fluid 26 of engine 10 using MCD 28 or another chip detector. Method 200 may be performed using system 30 described herein or using another system. Aspects of method 200 may be combined with method 100 or other steps described herein. Method 200 may also include aspects of system 30. In various embodiments, method 200 may include:

- detecting a presence of particle(s) 37 at MCD 28 immersed in lubrication fluid 26, particle(s) 37 providing electric communication between first terminal 36A and second terminal 36B of MCD 28 (blocks 202 and 204);
- after detecting the presence of particle(s) 37 at MCD 28, burning particle(s) 37 by Joule heating by continuously driving electric current through particle(s) 37 via first terminal 36A and second terminal 36B for a uninterrupted duration (block 206);
- determining an amount of energy consumed to burn particle(s) 37 by Joule heating (block 208);
- when the amount of energy is smaller than a prescribed energy value, determining that particle(s) are fuzz (block 210);
- when the amount of energy is greater than the prescribed energy value:
  - determining that the one or more particles are a chip (block 210); and
  - estimating a size of the chip based on the amount of energy consumed to burn the chip (block 212).

In some embodiments, method 200 or parts thereof may be conducted repeatedly in a continuous or intermittent manner. For example, at decision block 204, if resistance R1 is not indicative of particle(s) 37 bridging gap G between first terminal 36A and second terminal 36B, method 200 may return to block 202 where resistance R1 is measured. At decision block 210, if the energy consumed is indicative of particle(s) 37 being fuzz, method 200 may return to block 202 where resistance R1 is measured. After decision block 210, if the energy consumed is indicative of particle(s) 37 being a chip, the size of the chip may be estimated and method 200 may return to block 202 where resistance R1 is measured.

Whether the accumulated particle(s) 37 is/are fuzz or a chip, method 200 may include burning particle(s) 37 so that gap G between first terminal 36A and second terminal 36B may be at least partially cleared of particle(s) 37. This may allow system 30 to be ready to handle one or more subsequent accumulations of particle(s) 37 between first terminal 36A and second terminal 36B. Method 200 or parts thereof may be repeated with one or more additional accumulation of particle(s) 37.

Figure 6:
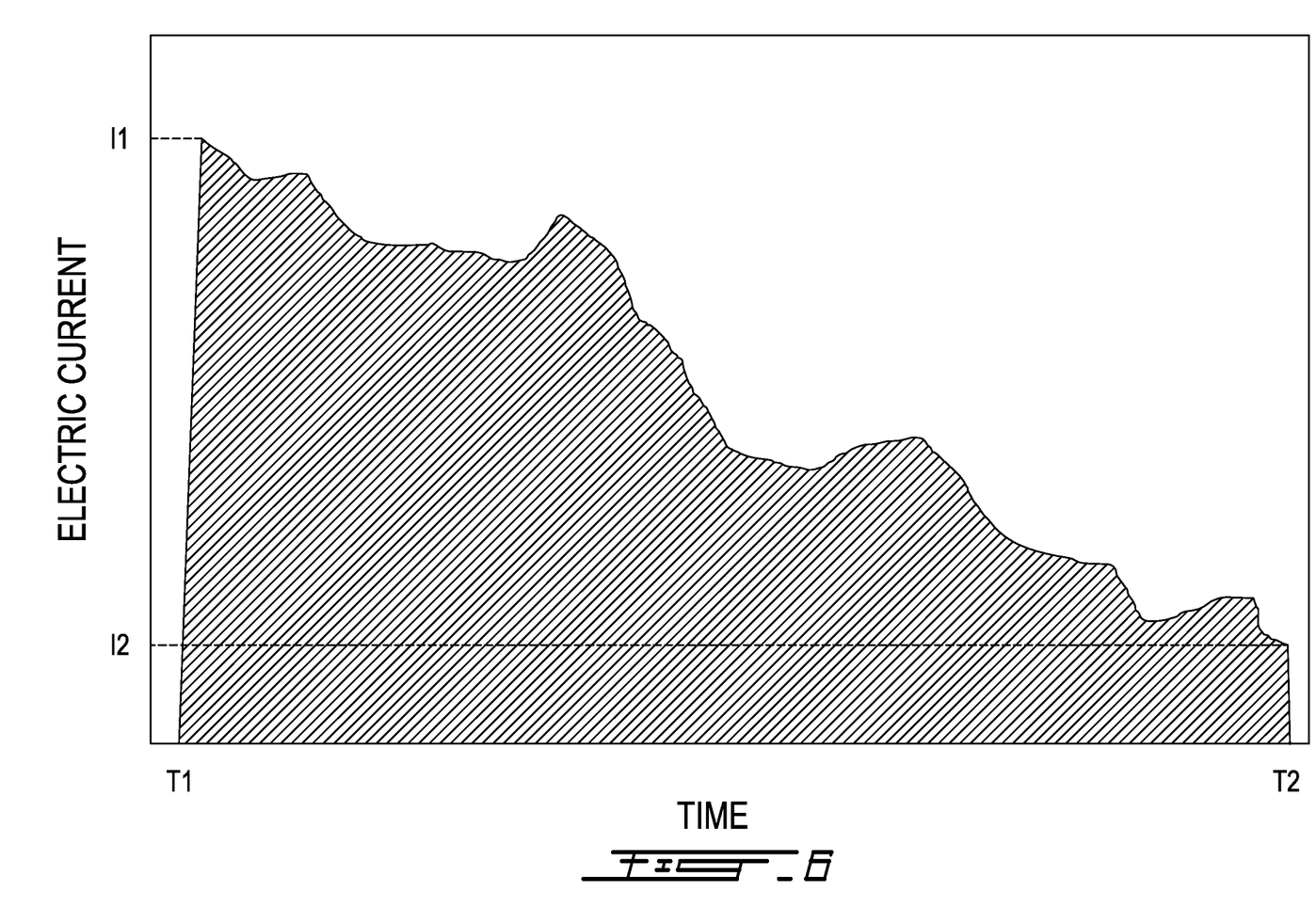
FIG. 6 is a graph of electric current driven through a chip during burning of the chip versus time.

FIG. 6 is a graph of exemplary electric current I driven through particle(s) 37 during burning of particle(s) 37 versus time. As explained above, the burning of particle(s) 37 may be performed using a single, uninterrupted delivery of electric current I having a duration (T2−T1) that is variable and suitable for achieving the desired burning of particle(s) 37. The continuous and uninterrupted Joule heating described herein may simplify the energy determination by eliminating the need to consider cooling and re-heating of particle(s) 37 that would otherwise occur during interruptions.

As explained above, electric current I may vary between first current I1 and second current I2 for example. First current I1 may be relatively high at the beginning of the current delivery when resistance R1 is relatively low. On the other hand, second current I2 may be relatively low toward the end of the current delivery when electric resistance R2 is relatively high.

FIG. 7 is an exemplary look-up table that may be used to define chip sizing relation 60 that may be used by system 30 and by methods 100, 200. Chip sizing relation 60 may include progressively increasing values E1-E4 of energy consumed to burn particle(s) 37 with a respective corresponding estimate of chip size. The values in chip sizing relation 60 may be determined empirically or by simulation/modelling based on specific operating conditions and parameters of system 30. The values in chip sizing relation 60 may also be based on preselected criteria (e.g., low and high threshold electric resistances) for detecting particle(s) 37 and for concluding the burning of particle(s) 37.

Chips may have more mass to be heated by Joule heating than fuzz and may therefore be associated with higher energy values than fuzz. For example, energy value E1 may be relatively low and may be associated with fuzz. When the energy consumed is indicative of particle(s) 37 being fuzz, no chip sizing may be required. On the other hand, energy values E2-E4 may be higher than energy value E1, and may be associated with burning progressively larger chips. When the energy consumed is indicative of particle(s) 37 being a chip, chip sizing may be performed to assist with assessing the health condition of engine 10.

FIG. 8 is an exemplary data record 62 constructed using the system 30. Data record 62 may be stored in memory 56 or elsewhere. Data record 62 may be constructed (e.g., populated) as (or after) particle(s) 37 are burned during the operation of system 30. Data record 62 may include a count (e.g., Chip Identification (ID) C1-C3) of the chips detected with associated values of energy consumed EC1-EC3 and/or associated values of chip sizes CS1-CS3. The data recorded in data record 62 may be used for trend analysis and health monitoring of engine 10.

The embodiments described in this document provide non-limiting examples of possible implementations of the present technology. Upon review of the present disclosure, a person of ordinary skill in the art will recognize that changes may be made to the embodiments described herein without departing from the scope of the present technology. Further modifications could be implemented by a person of ordinary skill in the art in view of the present disclosure, which modifications would be within the scope of the present technology.

What is claimed is:

1. A method of estimating a size of a chip in engine fluid of an engine, the method comprising:
   - detecting the chip at a magnetic chip detector immersed in the engine fluid, the chip providing electric communication between a first terminal and a second terminal of the magnetic chip detector;
   - after detecting the chip, burning the chip by Joule heating using a single continuous delivery of electric current through the chip via the first and second terminals of the magnetic chip detector, the single continuous delivery of electric current being of a duration for completing the burning of the chip, the single continuous delivery of electric current including a temporal variation in the electric current delivered through the chip, the single continuous delivery of electric current being terminated upon ceasing to detect the chip at the magnetic chip detector;
   - sensing the electric current delivered through the chip during the single continuous delivery of electric current to obtain a sensed electric current defining the temporal variation;
   - determining an amount of energy consumed to burn the chip in the single continuous delivery of electric current using the sensed electric current and the duration, and considering the temporal variation in the electric current delivered through the chip; and estimating the size of the chip based on the amount of energy consumed to burn the chip.

2. The method as defined in claim 1, comprising automatically initiating the burning of the chip by Joule heating after detecting the chip at the magnetic chip detector.

3. The method as defined in claim 2, wherein detecting the chip at the magnetic chip detector includes detecting, between the first and second terminals, an electric resistance at or below a resistance threshold.

4. The method as defined in claim 1, wherein detecting the chip at the magnetic chip detector includes detecting a short-circuit condition between the first and second terminals of the magnetic chip detector.

5. The method as defined in claim 1, comprising terminating the single continuous delivery of electric current when an electric resistance between the first and second terminals reaches or exceeds a resistance threshold.

6. The method as defined in claim 1, comprising terminating the single continuous delivery of electric current upon an occurrence of an open-circuit condition between the first and second terminals of the magnetic chip detector.

7. The method as defined in claim 1, wherein:
the chip is a first chip;
the method is repeated with a second chip; and
the method includes constructing a data record including a count of the first and second chips burned by Joule heating.

8. The method as defined in claim 1, wherein:
the chip is a first chip;
the method is repeated with a second chip; and
the method includes constructing a data record including respective identifications and associated amounts of energy consumed to burn the first and second chips burned by Joule heating.

9. The method as defined in claim 1, comprising, after estimating the size of the chip, initiating a maintenance activity for the engine based on the size of the chip.

10. The method as defined in claim 1, comprising:
after estimating the size of the chip, selecting a maintenance activity for the engine based on the size of the chip; and
performing the maintenance activity.

11. The method as defined in claim 1, wherein the temporal variation in the electric current includes a decrease in electric current delivered during the continuous delivery of electric current.

12. A method of detecting and sizing a chip in lubrication fluid of an engine, the method comprising:
detecting a presence of one or more particles at a magnetic chip detector immersed in the lubrication fluid, the one or more particles providing electric communication between a first terminal and a second terminal of the magnetic chip detector;
after detecting the presence of the one or more particles at the magnetic chip detector, causing disintegration of the one or more particles by Joule heating by continuously driving electric current through the one or more particles via the first and second terminals for a uninterrupted duration to deliver a single continuous delivery of electric current through the one or more particles via the first and second terminals of the magnetic chip detector to complete the disintegration of the one or more particles, the single continuous delivery of electric current including a temporal variation in the electric current delivered through the one or more particles;
sensing the electric current delivered through the one or more particles during the single continuous delivery of electric current to obtain a sensed electric current defining the temporal variation;
ceasing to drive the single continuous delivery of electric current through the one or more particles upon ceasing to detect the presence of the one or more particles at the magnetic chip detector;
determining an amount of energy consumed to cause disintegration of the one or more particles by Joule heating using the single continuous delivery of electric current and the uninterrupted duration, and considering the temporal variation in the electric current delivered through the one or more particles;
when the amount of energy is smaller than a prescribed energy value, determining that the one or more particles are fuzz; and
when the amount of energy is greater than the prescribed energy value:
determining that the one or more particles are a chip; and
estimating a size of the chip based on the amount of energy consumed to cause disintegration of the chip.

13. The method as defined in claim 12, comprising automatically initiating the disintegration of the one or more particles by Joule heating after detecting the presence of the one or more particles at the magnetic chip detector.

14. The method as defined in claim 13, wherein detecting the presence of the one or more particles at the magnetic chip detector includes detecting, between the first and second terminals, an electric resistance at or below a first resistance threshold.

15. The method as defined in claim 12, comprising, after estimating the size of the chip, selecting a maintenance activity for the engine based on the size of the chip.

16. A system for detecting and sizing a chip in lubrication fluid of an engine, the system comprising:
a magnetic chip detector immersible in a lubrication fluid of the engine, the chip detector including a first terminal and a second terminal spaced apart from the first terminal;
an electric power source connectable to the magnetic chip detector to apply a voltage between the first and second terminals of the magnetic chip detector;
one or more data processors; and
non-transitory machine-readable memory storing instructions executable by the one or more data processors and configured to cause the one or more data processors to:
detect a presence of one or more particles at the magnetic chip detector immersed in the lubrication fluid based on a sensed resistance between the first and second terminals of the chip detector;
after detecting the presence of the one or more particles at the magnetic chip detector, cause burning of the one or more particles by Joule heating using a single continuous delivery of electric current through the one or more particles via the first and second terminals of the magnetic chip detector for a duration until the burning of the chip is complete, the single continuous delivery of electric current including a temporal variation in the electric current delivered through the one or more particles;
determine an amount of energy consumed to burn the one or more particles in the single continuous delivery of electric current using the electric current and the duration, and considering the temporal variation in the electric current delivered through the one or more particles; and when the amount of energy consumed to burn the one or more particles is indicative of the one or more particles being a chip, estimate a size of the chip based on the amount of energy consumed to burn the one or more particles.

17. The system as defined in claim 16, wherein the instructions are configured to cause the one or more data processors to automatically initiate the burning of the one or more particles by Joule heating after detecting the presence of the one or more particles at the magnetic chip detector.

18. The system as defined in claim 16, wherein detecting the chip at the magnetic chip detector includes detecting, between the first and second terminals, an electric resistance at or below a resistance threshold.

19. The system as defined in claim 16, wherein the instructions are configured to cause the one or more data processors to terminate the single continuous delivery of electric current when the presence of one or more particles at the magnetic chip detector is no longer detected.

20. The system as defined in claim 16, wherein the instructions are configured to cause the one or more data processors to, after estimating the size of the chip, select a maintenance activity for the engine based on the size of the chip.

* * * * *